US00PP36117P2

(12) United States Plant Patent
Farrow

(10) Patent No.: US PP36,117 P2
(45) Date of Patent: Sep. 17, 2024

(54) ***CAMELLIA* PLANT NAMED 'FARROWCJH'**

(50) Latin Name: ***Camellia* hybrid**
Varietal Denomination: FARROWCJH

(71) Applicant: Spring Meadow Nursery, Inc., Grand Haven, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/541,331

(22) Filed: Dec. 15, 2023

(51) Int. Cl.
*A01H 5/02* (2018.01)
*A01H 6/00* (2018.01)

(52) U.S. Cl.
USPC ..... Plt./243
CPC ..... *A01H 6/00* (2018.05)

(58) Field of Classification Search
USPC ..... Plt./243
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Camellia* plant named 'FARROWCJH' is disclosed, characterized by large, double, magenta-pink flowers. Foliage is glossy dark green, with orange-red new growth. Plants are well-branched, with good container performance. The new cultivar is a *Camellia*, suitable for ornamental garden purposes.

3 Drawing Sheets

Latin name of the genus and species: *Camellia* hybrid.
Variety denomination: 'FARROWCJH'.

BACKGROUND OF THE INVENTION

The new cultivar is a product of a planned breeding program by the inventor, to produce new *Camellia* varieties with increased cold hardiness, improved habit, improved container performance, and longer blooming periods. The crossing resulting in the new cultivar was made during the fall of 2013, at a nursery in Warwick, Maryland. The seed parent is the unpatented variety *Camellia* 'Winter's Joy'. The pollen parent is the unpatented *Camellia* (*sasangua* x *hiemalis*) x *oleifera* 'Winter's Snowman'. The inventor discovered the new variety at the same nursery in October 2015.

Propagation of 'FARROWCJH' by hardwood vegetative cuttings was first performed in January 2015 at the same nursery in Warwick, Maryland. Multiple generations have been reproduced and have shown that the unique features of this cultivar are stable and reproduced true to type.

Date of the first public disclosure was Jun. 27, 2023, occurring in Grand Haven, Michigan. This disclosure was made directly by the inventor or one who obtained the claimed invention directly or indirectly from the inventor. This disclosure and all public disclosures made between Jun. 27, 2023 and the filing of this application fall within the exception allowed under 102(b)(1).

SUMMARY OF THE INVENTION

The cultivar 'FARROWCJH' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWCJH'. These characteristics in combination distinguish 'FARROWCJH' as a new and distinct *Camellia* cultivar:

1. Large, double, magenta-pink flowers.
2. Flat, saucer-like flower shape.
3. Hardiness USDA 7(6b)-9.
4. Attractive, healthy, glossy, dark green foliage.
5. Orange-red colored new growth.
6. Upright, well-branched habit which lends itself to good container performance.

COMPARISON TO PARENT CULTIVARS

'FARROWCJH' is similar in most horticultural characteristics to the seed parent variety *Camellia* 'Winter's Joy'. Plants of the new cultivar 'FARROWCJH' are similar to plants of the seed parent in most horticultural characteristics, however, differ in the following:

1. Petal color of the new variety is a darker, more saturated pink than the petal color of the seed parent.
2. Plant habit of the new variety is more compact, well-branched, and less rangy than the plant habit of the seed parent.
3. New growth of the new variety has an orange-red flush, while the new growth of the seed parent does not.

'FARROWCJH' is similar in most horticultural characteristics to the pollen parent variety *Camellia* (*sasangua* x *hiemalis*) x *oleifera* 'Winter's Snowman'. Plants of the new cultivar 'FARROWCJH' are similar to plants of the pollen parent in most horticultural characteristics, however, differ in the following:

1. Petal color of the new variety is magenta-pink, while the petal color of the pollen parent is white.
2. Plant habit of the new variety is more compact, well-branched, and less rangy than the plant habit of the pollen parent.

3. Foliage color of the new variety is a darker green than the foliage color of the pollen parent.

COMMERCIAL COMPARISON

'FARROWCJH' can be compared to the commercial variety *Camellia* 'Winter's Star', unpatented. Plants of the new cultivar 'FARROWCJH' are similar to plants of 'Winter's Star' in most horticultural characteristics, however, plants of the new cultivar 'FARROWCJH' differ in the following:

1. Petal color of the new variety is a darker, more saturated pink than the petal color of this comparator.
2. Plant habit of the new variety is more compact, well-branched, and less rangy than the plant habit of this comparator.
3. Plants of the new variety produce more buds and flowers per lateral branch than plants of this comparator.

BRIEF DESCRIPTION OF THE PHOTOGRAPHS

The accompanying photograph in FIG. 1 illustrates in full color a plant of 'FARROWCJH' grown outdoors in Grand Haven, Michigan.

Figure 1:
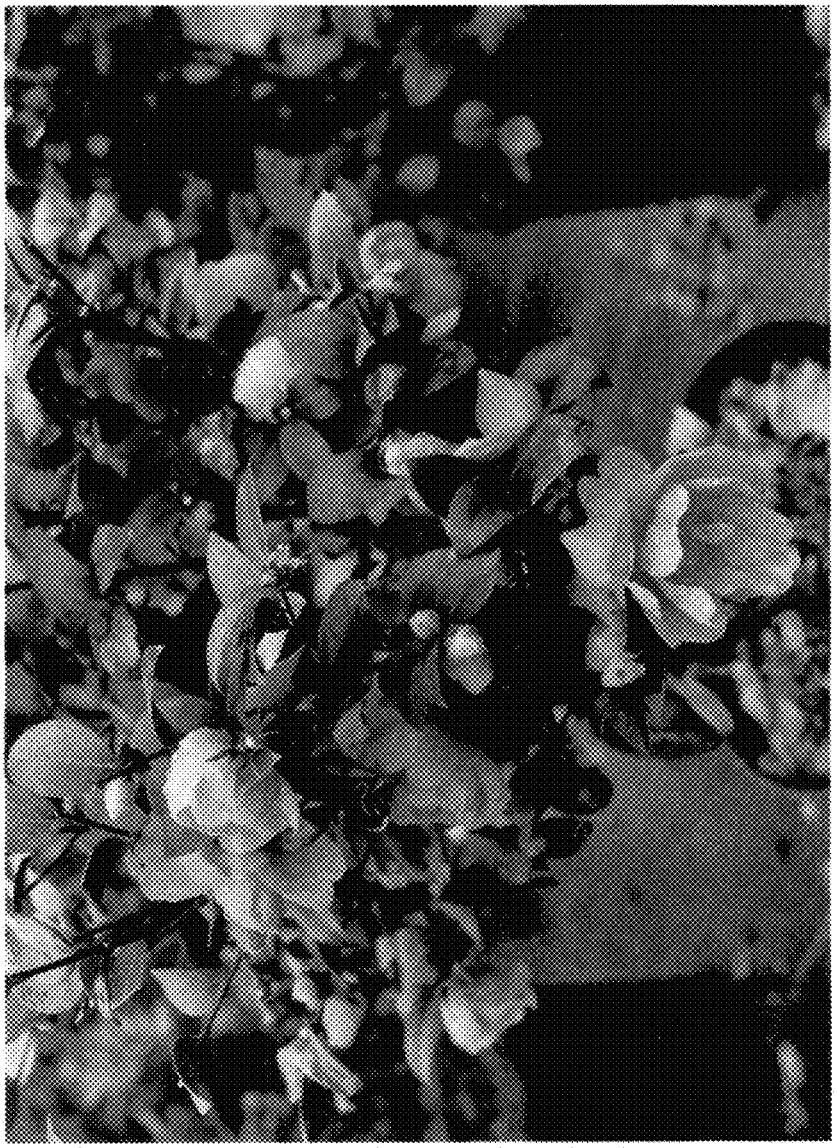
Figure 2:
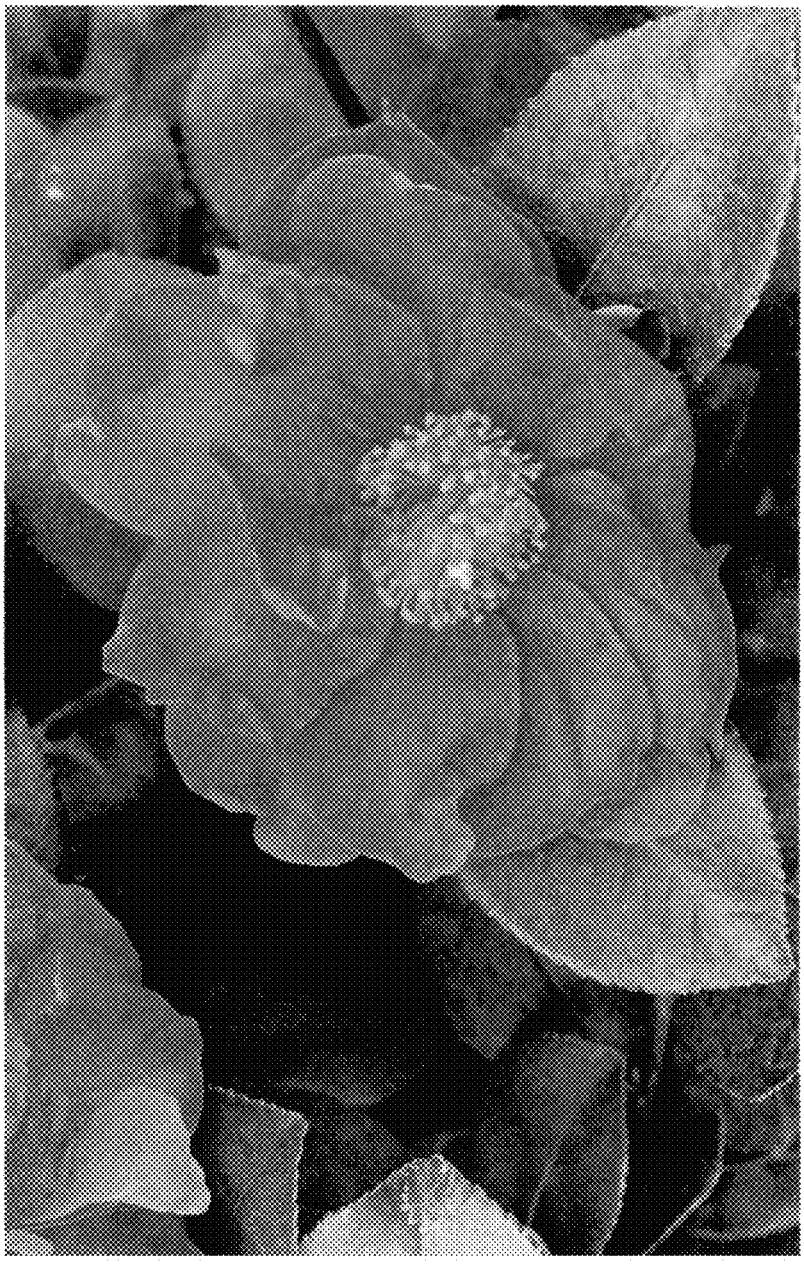
FIG. 2 is a close-up view of the flower of 'FARROWCJH'.
Figure 3:
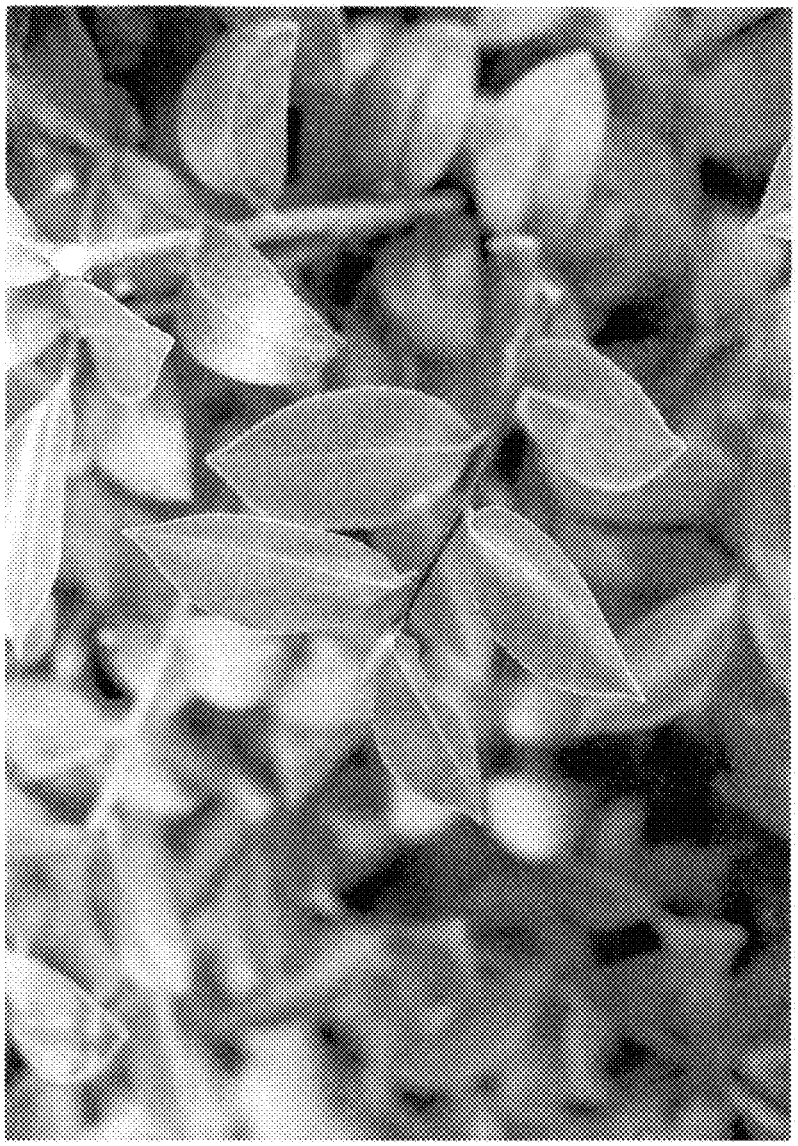
FIG. 3 shows a closer view of the new flush coloration on plants of the new variety. Plants photographed are approximately 4 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWCJH' plants grown in a poly-greenhouse in Grand Haven, Michigan in the fall of 2022. Plants are approximately 4 years old, in 3-gallon containers. The average day time temperature is 18-27° C., average night temperature is 5-10° C. Measurements and numerical values represent averages of typical plant types.

Botanical classification: *Camellia* hybrid 'FARROWCJH'.

PROPAGATION

Method: Hardwood cuttings.

Time to rooting: 4 weeks in summer at 18-27° C.

Root description: Moderately dense, freely branching, thin to medium thickness, and fibrous. Light brown to tannish-white in color, not accurately measured by The R.H.S. Color Chart.

PLANT

Plant type: Evergreen flowering shrub.

Plant shape: Upright.

Growth habit: Upwards and somewhat outwards.

Height: 140 cm.

Plant spread: 60 cm.

Growth rate: Moderate.

Plant vigor: Good.

Branching characteristics:

*Lateral Branches.*—Branching Habit: Basal; some pinching required. Quantity: 4 to 5 main stems with approximately 20 smaller branchlets. Length: Main Stems: 120 cm. Branchlets: About 40 cm. Diameter: 3 mm.

*Stem.*—Shape: Rounded. Aspect: 45° to 90°. Strength: Strong. Pubescence: None. Color: New Growth: Near RHS Greyed-Red 183B. Old Growth: RHS Grey-Brown 199A and N199B.

*Internode length.*—2.5 cm.

FOLIAGE

Leaf:

*Type.*—Single.

*Arrangement.*—Alternate.

*Length.*—4.5 cm.

*Width.*—3 cm.

*Shape.*—Elliptic.

*Apex.*—Acuminate.

*Base.*—Obtuse.

*Margin.*—Very slightly serrulate.

*Texture of top surface.*—Glabrous.

*Texture of bottom surface.*—Glabrous.

*Color.*—Young foliage upper side: RHS Yellow-Green 144B tinted Greyed-Orange 174C. Young foliage under side: RHS Yellow-Green 144B tinted Greyed-Orange 174C. Mature foliage upper side: Near RHS Green NN137A. Mature foliage under side: Between RHS Green NN137B and 137B.

*Venation.*—Type: Pinnate. Venation color upper side: Between RHS Green NN137B and 137B. Venation color under side: Between RHS Green NN137B and 137B.

Petiole:

*Length.*—5 mm.

*Diameter.*—2 mm.

*Texture, upper side.*—Glabrous.

*Texture, under side.*—Glabrous.

*Color.*—Between RHS Green NN137B and 137B.

FLOWER

Bloom period: Fall.

Flowers:

*Arrangement.*—Flowering at the terminal ends of lateral branches with buds typically emerging in pairs or groups of 3.

*Shape.*—Double whorl.

*Aspect.*—Outward.

*Quantity of flowers per lateral stem.*—About 5 per branchlet.

*Quantity of buds per lateral stem.*—About 5 per branchlet.

*Quantity of flowers and buds per plant.*—About 100.

*Length.*—9 cm.

*Diameter.*—9 cm.

*Depth.*—2.5 cm.

*Persistence.*—Self-cleaning.

*Fragrance.*—Mild to moderate intensity with notes of lemon peel and jasmine.

Petals:

*Length.*—4.75 cm.

*Width.*—3.5 cm.

*Apex.*—Obtuse or notched.

*Base*.—Obovate.
*Shape*.—Elliptic.
*Margin*.—Entire but sometimes with 1-2 irregularly placed notches (distinct from apex).
*Arrangement*.—Double whorl.
*Number*.—About 15.
*Fused*.—No.
*Appearance*.—Softly cupped/inwardly recurved with slight irregular wrinkling and slightly undulate margins.
*Texture*.—Glabrous, silky, both sides.
*Color*.—Upper surface at first opening: RHS Red-Purple 60D. Under surface at first opening RHS Red-Purple 60D. Upper surface at maturity: RHS Red-Purple 72D fading to Red-Purple 63B at base. Under surface at maturity: RHS Red-Purple 72D fading to Red-Purple 63B at base.

Petaloids:
*Length*.—2.5 cm.
*Width*.—2 cm.
*Apex*.—Notched.
*Base*.—Cuneate.
*Shape*.—Irregularly shaped, crumpled and crescent like.
*Margin*.—Sinuate and often with 1-2 irregularly placed notches (distinct from apex).
*Arrangement*.—Emerging as a loose whorl or singly from the center of the flower/anthers.
*Number*.—1 to 3.
*Fused*.—No.
*Appearance*.—Irregular and crumpled, sometimes crescent-shaped.
*Texture*.—Both sides glabrous, silky with crumpled texture.
*Color*.—Upper surface at first opening: RHS Red-Purple 60D. Under surface at first opening RHS Red-Purple 60D. Upper surface at maturity: RHS Red-Purple 72D fading to Red-Purple 63B at base. Under surface at maturity: RHS Red-Purple 72D fading to Red-Purple 63B at base.

Bud:
*Shape*.—Ovoid.
*Length*.—1.5 cm.
*Diameter*.—1.25 cm.
*Color*.—RHS Yellow-Green N144A to 144B and 144C with silvery-white pubescence.

Sepals: Absent—calyx sheds upon bud break.

Peduncle:
*Length*.—2 mm.
*Diameter*.—2 mm.
*Color*.—RHS Yellow-Green 144B.
*Texture*.—Glabrous.
*Aspect*.—45° relative to stem.
*Strength*.—Good.

REPRODUCTIVE ORGANS

Stamens:
*Number*.—About 100.
*Filament length*.—1.25 cm.
*Filament color*.—RHS Yellow 8B to 8C.
*Anthers*.—Length: 2 mm. Color: RHS Yellow 8B. Pollen: Quantity: Plentiful. Color: RHS Yellow 9A. Shape: Club-like.

Pistil:
*Number*.—1.
*Length*.—1 cm.
*Style*.—Length: 0.75 cm. Color: RHS Yellow-Green 145D.
*Stigma*.—Shape: Linear, pistil split into 3. Color: RHS Yellow-Green 145D.

OTHER CHARACTERISTICS

Disease and pest resistance: Neither resistance nor susceptibility to normal pests of *Camellia* observed.
Temperature tolerance: USDA Zone 7(6b)-9.
Fruit/seed: Not observed.

What is claimed is:

1. A new and distinct cultivar of *Camellia* plant named 'FARROWCJH' as herein illustrated and described.

* * * * *